United States Patent
Fukuchi

[11] Patent Number: 5,888,488
[45] Date of Patent: Mar. 30, 1999

[54] HAIR COSMETIC COMPOSITION

[75] Inventor: Yoshihiko Fukuchi, Yokohama, Japan

[73] Assignee: Shiseido Company Ltd., Tokyo, Japan

[21] Appl. No.: 816,202

[22] Filed: Mar. 20, 1997

Related U.S. Application Data

[63] Continuation of Ser. No. 151,042, Nov. 12, 1993, abandoned, which is a continuation of Ser. No. 855,743, Mar. 23, 1992, abandoned.

[30] Foreign Application Priority Data

Apr. 1, 1991 [JP] Japan .................................. 3-068338

[51] Int. Cl.$^6$ .............................. A61K 7/06; A61K 7/07
[52] U.S. Cl. ...................................... 424/70.12; 424/70.28
[58] Field of Search .............................. 424/70.12, 70.28, 424/70.1

[56] References Cited

U.S. PATENT DOCUMENTS

| | | | |
|---|---|---|---|
| 5,102,655 | 4/1992 | Yoshihara et al. ..................... | 424/72 |
| 5,104,646 | 4/1992 | Bolich, Jr. et al. ..................... | 514/781 |
| 5,120,531 | 6/1992 | Wells et al. ............................. | 424/70 |
| 5,482,703 | 1/1996 | Pings ..................................... | 454/70.12 |

FOREIGN PATENT DOCUMENTS

| | | |
|---|---|---|
| 56-169614 | 12/1981 | Japan . |
| 61-6 | 1/1986 | Japan . |
| 61-286311 | 12/1986 | Japan . |
| 63-222109 | 9/1988 | Japan . |

*Primary Examiner*—Sally Gardner-Lane
*Attorney, Agent, or Firm*—Foley & Lardner

[57] ABSTRACT

A hair cosmetic composition comprising, as components of this hair cosmetic composition, (A) a mono-long chain alkyl quaternary ammonium salt, (B) a higher alcohol having a straight alkyl group having 14 to 22 carbon atoms and (C) a high molecular weight silicone which is gelled at normal temperature, the molar ratio of (B) relative to (A) being within the range of from 3 to 15, and containing the respective components (A), (B) and (C) at specific ratios in the above cosmetic composition.

17 Claims, No Drawings

HAIR COSMETIC COMPOSITION

This application is a continuation of application Ser. No. 08/151,042, filed Nov. 12, 1993, now abandoned which is a continuation of Ser. No. 07/855,743 filed on Mar. 23, 1992 now abandoned.

BACKGROUND OF THE INVENTION

1. Field of the Invention

The present invention relates to a hair cosmetic composition, and more particularly, to a hair cosmetic composition capable of imparting an excellent smoothness and luster to hair, without making the hair sticky, an providing an excellent protection of hair from physical damage caused by, for example, brushing.

2. Description of the Related Art

Hair cosmetic compositions used as a rinse, to impart a smoothness and luster to hair and improve the combing of hair, are commercially available as, for example, a hair rinse, hair treatment, and hair conditioner. These hair cosmetic compositions generally have quaternary ammonium salts formulated therein, and it is known that the rinsing effect mentioned above is obtained by an adsorption of these salts by the hair. Further, to improve the feeling after use, such as the smoothness, luster and wetness, oil components such as higher alcohols, glycerol mono-fatty acid esters, higher fatty acids, liquid paraffins, solid paraffins, ester oils, and silicone oils with polymerization degrees of 3 to 650, are added. Namely, these respective components are used to obtain hair cosmetic compositions imparting a smoothness to the hair without making the hair sticky.

For example, Japanese Unexamined Patent Publication (Kokai) NO. 61-286311 discloses a hair cosmetic composition in which a mixed component of a quaternary ammonium salt and a higher alcohol, also a part of the components used in the present invention when combined at a specific ratio, and a low viscosity oil component are incorporated in specific amounts, respectively, to give an excellent smoothness without stickiness. Also, Japanese Unexamined Patent Publication (Kokai) No. 63-222109 discloses a hair cosmetic composition comprising the above quaternary ammonium salt and a high molecular weight silicone belonging to the category of silicone gum, at specific ratios, to give the hair an excellent washing resistance.

The prior arts mentioned above have achieved some improvements in the hair cosmetic compositions. For example, in Japanese Unexamined Patent Publication No. 63-222109, a softness, smoothness and a luster imparting effect to the hair are exhibited along with an improvement of the washing resistance thereof, but this does not discount the need for a hair cosmetic composition with a further improved smoothness, softness and luster imparting effect. For example, even if a smoothness can be imparted without stickiness during the coating and rinsing of these hair cosmetic compositions, it does not necessarily follow that satisfactory characteristics can be exhibited during the drying of the hair or thereafter.

SUMMARY OF THE INVENTION

Accordingly, an object of the present invention is to eliminate the above-mentioned problems of the prior art and to provide a hair cosmetic composition having a further enhanced smoothness, softness and luster imparting effect, without losing the advantages possessed respectively by the compositions of the prior art.

The other objects and advantages of the present invention will be apparent from the descriptions mentioned hereinbelow.

In accordance with the present invention, there is provided a hair cosmetic composition comprising:

(A) at least one quaternary ammonium salt having the formula (I):

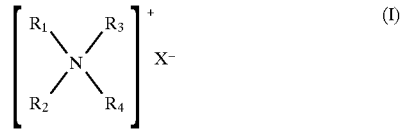

wherein $R_{11}$ represents an alkyl group or hydroxyalkyl group having 14 to 22 carbon atoms, $R_2$, $R_3$ and $R_4$ independently represent an alkyl group or hydroxyalkyl group having 1 to 3 carbon atoms or a benzyl group, X represents a halogen atom or an alkyl sulfuric acid group having 1 to 2 carbon atoms;

(B) a higher alcohol having a straight alkyl group having 14 to 22 carbon atoms; and (C) at least one high molecular weight silicone having the formula (II):

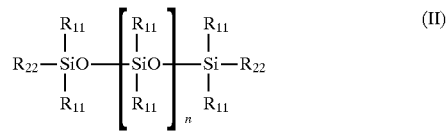

wherein $R_{11}$ represents a methyl group or a part thereof may also represent a phenyl group, $R_{22}$ represents a methyl group or a hydroxy group, and n is an integer of 3,000 to 20,000, the amount of the component (A) being within the range of from 0.1 to 5.0% by weight, based on the total weight of the hair cosmetic composition, the mole ratio of the component (B) relative to the component (A) being within the range of from 3 to 15, and the amount of the component (c) being within the range of from 0.1 to 10% by weight, based on the total weight of the hair cosmetic composition.

DESCRIPTION OF THE PREFERRED EMBODIMENTS

The present inventors have studied various combinations of the existing hair cosmetic composition components, and consequently, have found that the effect obtained by the combination of the quaternary ammonium salt and the higher alcohol disclosed by Japanese Unexamined Patent Publication (Kokai) No. 61-286311 will not be adversely affected if mixed with the high molecular weight silicone disclosed by Japanese Unexamined Patent Publication (Kokai) No. 63-222109, and Unexamined Patent Publication (Kokai) No. 63-222109, and indeed, will synergetically enhance the effect of the high molecular weight silicone, to thus accomplish the present invention.

The quaternary ammonium salt of the component (A) usable in the present invention is of the above formula (I) wherein the group $R_1$ is an alkyl group having 14 to 22 carbon atoms, such as a cetyl group, stearyl group, and behenyl group. The hydroxyalkyl group having 14 to 22 carbon atoms, preferably 16 to 22 carbon atoms, of the group $R_1$, is, for example, a 12-hydroxystearyl group. As the group $R_1$, an alkyl group having 16 to 22 carbon atoms is preferable, and particularly preferable are a stearyl group and a behenyl group. The groups $R_2$, $R_3$ and $R_4$ are independently alkyl groups or hydroxyalkyl groups having 1 to 3 carbon atoms, and preferable groups include a methyl group, ethyl group, propyl group, hydroxymethyl group, and hydroxyethyl group. The groups $R_2$, $R_3$ and $R_4$ may be either the same or different groups, and the halogen atom or the group X is preferably a chlorine atom or bromine atom.

Examples of the quaternary ammonium salt represented by the above-mentioned formula (I) are cetyltrimethylammonium chloride, stearyltrimethylammonium chloride, behenyltrimethylammonium chloride, behenyldimethylhydroxyethylammonium chloride, stearyldimethylbenzylammonium chloride, and cetyltriethylammoniummethyl sulfate. Among these, particularly preferable are stearyltrimethylammonium chloride, behenyltrimethylammonium chloride, stearyldimethylbenzylammonium chloride, and mixtures thereof.

The above-mentioned component (B) usable in the present invention is a higher alcohol having a straight alkyl group having 14 to 22 carbon atoms. As the preferable component (B), there are included straight higher alcohols having 16 to 22 carbon atoms, such as cetyl alcohol, stearyl alcohol, behenyl alcohol, and other aliphatic alcohols.

The high molecular weight silicone of the component (C) usable in the present invention also may be mixed with at least one compound represented by the above-mentioned formula (II). These compounds generally exhibit soft rubbery properties at normal temperature. The specific structures represented in terms of chemical names (or general names) include dimethylpolysiloxane, methylphenylpolysiloxane, terminal hydroxy containing dimethylpolysiloxane, and terminal hydroxy containing methylphenylpolysiloxane.

In the hair cosmetic composition of the present invention, it is necessary to formulate the respective components (A), (B) and (C) described above in a specific quantitative relationship.

The component (A) comprising at least one quaternary ammonium salt having the above-mentioned formula (I) should be formulated in an amount within the range of from 0.1 to 5.0% by weight, preferably from 0.6 to 3.0% by weight. When the amount formulated is less than 0.1% by weight, a sufficient rinsing effect as the hair cosmetic composition cannot be obtained. When the amount formulated exceeds 5.0% by weight, the viscosity of the hair cosmetic composition will become undesirably high.

The above-mentioned component (B) must be formulated in an amount corresponding to a mole ratio of the component (B) relative to the component (A), i.e., (B)/(A), of 3 to 15. The above mole ratio is preferably within the range of from 3.5 to 10. In this connection, for example, Japanese Unexamined Patent Publication (Kokai) No. 63-222109 discloses a composition containing a higher alcohol corresponding to the component (B) in the present invention, as an optional component in addition to the quaternary ammonium salt as described above, and the high molecular weight silicone substantially equal to the component (C) in the present invention, which are essential components thereof. In these compositions, the mole ratio of the higher alcohol relative to the quaternary ammonium salt, i.e., (B)/(A), is less than 0.5, and there is no suggestion therein that an addition of a higher alcohol exhibits a specific effect.

Thus, the present invention is distinguished from the prior art not only by using the compound of the formula (I) and the higher alcohol in the mole ratio as specified above, but also in that it exhibits the excellent characteristics described below, due to the combination thereof with the high molecular weight silicone. In more detail, the effect of using the quantitative relationship of the components (A), (B) and (C) as defined in the present invention is obtained by choosing the specific mole ratio of the component (A) to the component (B) described above as for the formation of a specific gel phase as described in the Japanese Unexamined Patent Publication (Kokai) No. 61-286311, which greatly enhances the amounts of these components adsorbed by the hair. Further, surprisingly, it is considered that not only will the addition of the high molecular weight silicone having the formula (II) to the gel phase not obstruct a stabilization of the gel phase, but also it will serve to assist in a close adsorption of the high molecular weight silicone onto hair while simultaneously preventing an elimination of the above components (A) and (B) from the hair. Such an effect will synergetically impart an excellent smoothness to the hair, without making it sticky, during a rinsing of hair, during drying or after drying, when using the hair cosmetic composition of the present invention, thus providing an enhanced protection of the hair from damage caused by brushing, etc., and at the same time, imparting an excellent luster (gloss) to hair and preventing the generation of split hairs.

The amount of the component (C) having the above formula (II), to be formulated in order to exhibit such effects, is 0.1 to 10% by weight, preferably 0.2 to 8% by weight, based on the total weight of the hair cosmetic composition. When this amount is less than 0.1% by weight, a satisfactory effect cannot be obtained, and conversely, when this amount is in excess of 10% by weight, the solubility of the component (C) is undesirably worsened.

When formulating the high molecular weight silicone of the present invention in the hair cosmetic composition, desirably it is formulated in the form of a solution dissolved in a liquid oil. Note, it may, of course, be added separately to the hair cosmetic composition and dissolved in the system.

The liquid oil may include, for example, linear silicones, cyclic silicones or isoparaffinic hydrocarbons.

The above-mentioned linear silicones can be represented by the following formula.

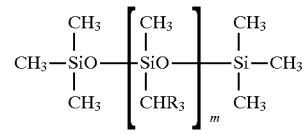

wherein m represents an integer of 0 to 650.

The cyclic silicones can be represented by the following formula.

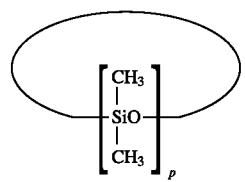

wherein p represents an integer of 3 to 7.

Specific examples of these compounds include those known under the following general names, i.e., octamethylcyclotetramethylsiloxane, decamethylcyclopentasiloxane and tetradecamethylcyclohexasiloxane.

Examples of isoparaffinic hydrocarbons are those having boiling points ranging from 60° to 260° C. under normal pressure, as exemplified by Isopar A (registered trademark), Isopar C, D, E, G, H, K, L, M produced by Exon Co., Shellsol 71 (trademark) produced by Shell Co., Soltol 100 (trademark) or Soltol 130, 220 produced by Philips Co.

The low boiling oil as described above can be used either alone or as a combination of two or more kinds thereof, but preferably is used in a total amount of 1 to 50-fold (by weight) of the high molecular weight silicone, more preferably 10 to 80% by weight of the total amount of the hair cosmetic composition.

In the hair cosmetic composition of the present invention, any desired formulation component conventionally used in hair cosmetic compositions can be added, within the range which will not adversely affect the effects to be obtained by the present invention. Examples of these formulation components include oily components other than the above-mentioned component (C) of the present invention, such as solid paraffin or ester oil; humectants, such as propylene glycol or glycerine; water-soluble polymeric substances, such as methylcellulose or hydroxyethylcellulose; nonionic surfactants, such as polyoxyethylene hardened castor oil or polyoxyethylene alkyl ether; amphoteric surfactants, such as 2-alkyl-N-carboxymethyl-N-hydroxyethylimidazolinium betaine or trialkylaminoacetic betaine; natural extracts of animals and vegetables and derivatives thereof; organic acids, such as citric acid or lactic acid; inorganic salts, such as sodium chloride or potassium chloride; perfumes and pigments; preservatives such as paraben; chelating agents such as EDTA-3 Na; and UV-ray absorbers, such as oxybenzone.

The term "hair cosmetic composition" of the present invention means any cosmetic composition usable for the hair, particularly a cosmetic composition for imparting a conditioning effect to hair, for example, cosmetic compositions including a rinsing step with water, such as a hair rinse, hair treatment, and hair pack.

EXAMPLES

The present invention is now described in more detail with reference to Examples, to which the present invention is in no way limited. In the following Examples, "%" represents % by weight unless otherwise specified. Also, in the following Examples, the hair protective effects and the organoleptic evaluations in the respective samples were carried out according to the standards shown below.

(1) Hair protective effect

One gram of each sample was coated on a bundle of 500 to 600 hairs 15 cm in length, and after a rinsing by shaking (100 cycles) in 300 ml of lukewarm water at 40° C. was repeated twice, the hair bundle was dried. Brushing of the hair bundle was repeated with a constant force, and after 20,000 strokes with a brush, the number of split hairs and torn hairs were counted, and the generation ratios based on the total number of split hairs and torn hairs were calculated.

Relative to the generation ratio X% of split hairs and torn hairs in untreated hair, the generation ratios Y% in the treated hair of the respective samples were compared, and the following evaluations were made according to the values of Y/X.

| | | |
|---|---|---|
| Y/X < 0.5 | A | large hair protective effect |
| 0.5 ≦ Y/X < 0.8 | B | medium hair protective effect |
| 0.8 ≦ Y/X < 1.0 | C | little hair protective effect |
| 1.0 ≦ Y/X | D | no hair protective effect |

(2) Measurement of amount adsorbed onto hair

Two grams of each sample were coated on 4 g of a bundle of hairs, after a complete defatting thereof, and after a rinsing by shaking (100 cycles) in one liter of lukewarm water (40° C.) was repeated twice, the hair bundle was dried. The adsorbed substances were soxhlet-extracted (dichloromethane/methanol=92/8 vol.%, 5 hrs extraction) from each hair bundle, and the sample amount adsorbed per one gram of the hair was calculated from the weight thereof. The adsorbability of each sample by the hair was evaluated as shown below.

| Amount of sample adsorbed per 1 g of hair | | Evaluation |
|---|---|---|
| 30 mg or more | A | large adsorbability by the hair |
| 10 to 30 mg | B | medium adsorbability by the hair |
| 10 mg or less | C | little adsorbability by the hair |

(3) Hair luster imparting effect

One gram of each sample was coated on a bundle of 500 to 600 hairs 15 cm in length, and after a rinsing by shaking (100 cycles) in 300 ml of lukewarm water of 40° C. was repeated twice, the hair bundle was dried. Ten hairs were chosen arbitrarily from the hair bundle, and the reflected light distribution relative to the incident light was measured by a bending photometer (produced by Murakami Shikisai Kenkyujo) and the degree of gloss (luster) of the hair was determined according to the following formula.

$$G = \frac{s}{d} \quad \begin{array}{l} G\text{: degree of gloss} \\ s\text{: square reflected light dose} \\ d\text{: diffused light dose} \end{array}$$

According to the degree of gloss G determined as described above, the luster imparting effect to the hair of each sample was evaluated as follows.

| G | | Evaluation |
|---|---|---|
| 15 or more | A | large luster imparting effect |
| 10 to 15 | B | medium luster imparting effect |
| 5 to 10 | C | little luster imparting effect |
| 5 or less | D | no luster imparting effect |

(4) Uniform coatability

A uniform coatability was evaluated from a scanning electron microscope (SEM) photograph of a hair sample prepared in the same manner as for the measurement of the luster of the hair. The SEM photograph (400 to 1000-fold) of the hair treated with each sample was compared with an SEM photograph of the untreated hair, by 15 members of a panel, and the uniform coatability was evaluated according to the two rankings of "good" and "similar". From the results, the following evaluations were made.

| Evaluation results | Evaluation |
|---|---|
| one to which all 15 members answered "good" | A |
| one to which 8 to 14 of the 15 members answered "good" | B |
| one to which 7 or less of the 15 members answered "good" | C |

(5) Organoleptic evaluation of the effect to hair

As the subjects to be tested, 15 women 19 to 36 years old were chosen. The hair of each test subject was applied with each 12 g of the respective samples, after washing with a commercially available shampoo (conventional alkyl sulfate salt type shampoo), and after rinsing with water at about 40° C., and the feel of the hair during and after drying with a dryer was evaluated according to four rankings of "very good", "good", "similar" and "inferior" in comparison with a Control sample (comprising 2.0% of stearyltrimethylammonium chloride, 3.0% of cetostearyl alcohol, 5.0% of propylene glycol, and 90% of water). The following evaluations were made from these evaluation results.

| Evaluation results | Evaluation |
|---|---|
| one to which 12 or more of the 15 members answered "very good" or "good" | A |
| one to which 8 to 11 of the 15 members answered "very good" or "good" | B |
| one to which 4 to 7 of the 15 members answered "very good" or "good" | C |
| one to which 3 or less of the 15 members answered "very good" or "good" | D |

Example 1

Hair rinses were prepared according to the compositions shown in Table I, and the results of the evaluation thereof according to the standards described above are shown therein.

(mole ratio) must be in the range of from 3 to 15. Even if a high molecular weight silicone is formulated as the component (C), when the above ratio is within 3 (Control samples No. 3 and No. 5), it is clear that both a smoothness and a hair protective effect will not be exhibited.

When the above mole ratio exceeds 15, a problem of stability will arise in that crystals of a higher alcohol are precipitated.

Also, in the present invention, the quaternary ammonium salt must be the mono-long chain alkyl type, as when distearyldimethylammonium chloride (Control sample No. 4) is used, no smoothness is imparted to the hair.

Example 2

Hair rinses were prepared in a conventional manner according to the compositions shown in Table 2, and the results of the evaluation thereof as described above are shown therein.

TABLE I

| | | Control Sample | | | | | Samples of the Invention | | | |
|---|---|---|---|---|---|---|---|---|---|---|
| | Sample No. | 1 | 2 | 3 | 4 | 5 | 1 | 2 | 3 | 4 |
| Composition % by weight | Stearyltrimethylammonium chloride | 2.0 | 2.0 | 2.0 | 1.0 | 1.0 | 1.0 | 1.0 | 1.0 | 1.0 |
| | Distearyldimethylammonium chloride | — | — | — | 2.0 | — | — | — | — | — |
| | Cetostearyl alcohol ($C_{16}/C_{10}$ = 7/3) | 3.0 | 3.0 | 3.0 | 6.0 | 1.5 | 2.88 | 3.60 | 7.20 | 10.8 |
| | Dimethylpolysiloxane ($R_{11}$ and $R_{22}$ are methyl groups, n = 7000) | — | — | 2.0 | 2.0 | 3.0 | 2.0 | 2.0 | 2.0 | 2.4 |
| | Dimethylpolysiloxane ($R_{11}$ and $R_{22}$ are methyl groups, n = 1000) | — | 2.0 | — | 2.0 | — | — | — | — | — |
| | Dimethylpolysiloxane 5 cs | 10.0 | 10.0 | 10.0 | 10.0 | 10.0 | 10.0 | 10.0 | 10.0 | 10.0 |
| | Methyl paraben | q.s. | q.s. | q.s. | q.s. | q.s. | q.s. | q.s. | q.s. | q.s. |
| | Pigment | " | " | " | " | " | " | " | " | " |
| | Perfume | " | " | " | " | " | " | " | " | " |
| | Deionized water | Amount needed to make up the total to 100% | | | | | | | | |
| Quantitative relationship | Cetostearyl alcohol/Stearyltrimethylammonium chloride (mole ratio) | 2.08 | 2.08 | 2.08 | — | 2.08 | 4.0 | 5.0 | 10.0 | 15.0 |
| Physical properties | Hair protective effect | D | D | C | D | C | A | A | A | A |
| | Smoothness during rinsing | C | C | C | D | C | B | A | A | B |
| | Smoothness after drying | C | D | B | D | B | A | A | A | A |
| | Adsorbability by hair | C | B | B | C | C | A | A | A | A |
| | Luster imparting effect to hair | C | C | C | C | C | A | A | A | A |
| | Uniform coatability | C | C | C | C | C | A | A | A | A |

As can be seen from Table I, in the present invention, the cetostearyl alcohol/stearyltrimethyl-ammonium chloride

TABLE II

| | | Control Sample | | | | Samples of the Invention | | | | | | |
|---|---|---|---|---|---|---|---|---|---|---|---|---|
| | Sample No. | 1 | 2 | 3 | 4 | 1 | 2 | 3 | 4 | 5 | 6 | 7 |
| Composition % by weight | Cetyltrimethylammonium chloride | — | — | — | — | — | — | — | — | 2.0 | — | 1.0 |
| | Stearyltrimethylammonium chloride | 1.0 | 1.0 | 1.0 | 1.0 | 1.0 | 1.0 | 1.0 | 1.0 | — | — | — |
| | Behenyltrimethylammonium chloride | — | — | — | — | — | — | — | — | — | 0.5 | 1.0 |
| | Cetostearyl alcohol ($C_{16}/C_{18}$ = 7/3) | 3.6 | 3.6 | 3.6 | 3.6 | 3.6 | 3.6 | 3.6 | 3.6 | 12.5 | 3.1 | 7.01 |
| | Dimethylpolysiloxane ($R_{11}$ is a methyl group, $R_{22}$ is a hydroxyl group, n = 5000) | — | — | — | — | 5.0 | 4.0 | 2.0 | 5.0 | 8.0 | 0.1 | — |
| | Methylphenylpolysiloxane | — | — | — | — | — | 1.0 | — | — | — | — | 2.0 |

TABLE II-continued

| | Sample No. | Control Sample | | | | Samples of the Invention | | | | | | |
|---|---|---|---|---|---|---|---|---|---|---|---|---|
| | | 1 | 2 | 3 | 4 | 1 | 2 | 3 | 4 | 5 | 6 | 7 |
| | (10% of $R_{11}$ is a phenyl group and the balance is a methyl group) | | | | | | | | | | | |
| | Isopar H (note 1) | — | — | — | — | — | — | 10.0 | — | 25.0 | — | 10.0 |
| | Cyclic silicone pentamer | 20.0 | 20.0 | 20.0 | 20.0 | — | 15.0 | — | 20.0 | — | 10.0 | — |
| | Dimethylpolysiloxane ($R_{11}$ and $R_{22}$ are methyl groups, n = 2000) | 5.0 | — | — | — | — | — | — | — | — | — | — |
| | Squalane | — | 5.0 | — | — | — | — | — | — | — | — | — |
| | Cetyl 2-ethylhexanoate | — | — | 5.0 | — | — | — | — | — | 0.5 | — | — |
| | Dimethylpolysiloxane 20 cs | — | — | — | 5.0 | 20.0 | — | — | — | — | 10.0 | — |
| | Propylene glycol | 5.0 | 5.0 | 5.0 | 5.0 | 5.0 | 5.0 | 5.0 | 5.0 | 5.0 | 5.0 | 5.0 |
| | Methyl paraben | q.s. | q.s. | q.s. | q.s. | q.s. | q.s. | q.s. | q.s. | q.s. | q.s. | q.s. |
| | Pigment | " | " | " | " | " | " | " | " | " | " | " |
| | Perfume | " | " | " | " | " | " | " | " | " | " | " |
| | Deionized water | Amount needed to make up the total to 100% | | | | | | | | | | |
| Quantitative relationship | Higher alcohol/ Mono-long chain alkyl type quaternary ammonium salt (mole ratio) | 5.0 | 5.0 | 5.0 | 5.0 | 5.0 | 5.0 | 5.0 | 5.0 | 5.0 | 5.0 | 5.0 |
| Physical properties | Smoothness after drying | B | B | B | B | A | A | A | A | A | B | A |
| | Hair protective effect | D | D | D | D | A | A | A | A | A | A | A |
| | Adsorbability by hair | B | B | B | B | A | A | A | A | A | A | A |
| | Luster imparting effect to hair | C | C | C | C | A | A | A | A | A | B | A |
| | Uniform coatability | C | C | C | C | A | A | A | A | A | B | A |

(note 1): Soft liquid isoparaffin commercially available from Exon Co.

As apparent from Table II, the high molecular weight silicone of the component (C) of the present invention must have a polymerization degree n of 3,000 or more, and when a silicone with a polymerization degree n of less than 3,000 is used (Control samples No. 1 and No. 4), the smoothness after drying and the hair protective effect were both found to be unsatisfactory.

Also, a satisfactory result could not be obtained when formulating oil components other than the silicone generally formulated in hair rinses (Control samples No. 2 and No. 3). In contrast, when silicones with a polymerization degree n of 3,000 or higher are formulated, satisfactory results could be obtained for both the smoothness after drying and the hair protective effect, at formulation ratios thereof of 0.1% or higher.

Example 3

A hair rinse with the recipe shown below was prepared, and evaluated according to the same methods as used in Example 1 and Example 2.

| Component | % by weight |
|---|---|
| Cetyltrimethylammonium chloride | 0.6 |
| Stearyl alcohol ($C_{16}/C_{18}$ = 6/4) | 0.4 |
| Dimethylpolysiloxane ($R_{11}$ is methyl group, $R_{22}$ is hydroxyl group, n = 3000) | 3.0 |
| Cyclic silicone pentamer | 15.0 |
| Glycerol monostearate | 1.0 |
| Stearic acid | 0.5 |
| Glycerol | 5.0 |
| Propylene glycol | 5.0 |
| Yellow No. 4 (pigment) | q.s. |
| Perfume | q.s. |
| Methyl paraben | q.s. |
| EDTA-3 Na (chelating agent) | q.s. |
| Deionized water | Balance |

The hair rinse, in which the straight higher alcohol/mono-long chain alkyl type quaternary ammonium salt (molar ratio) is 8.43 and 3.0% of dimethylpolysiloxane where n=3000 is contained had an excellent stability, provided an excellent smoothness of the hair not found in the prior art by the organoleptic test evaluation, and imparted an excellent protective effect to the hair.

Example 4

A hair treatment cream with the recipe shown below was prepared, and evaluated according to the same methods as in the respective Examples shown above.

| Component | % by weight |
|---|---|
| Behenyltrimethylammonium chloride | 3.0 |
| Cetostearyl alcohol ($C_{16}/C_{18}$ = 7/3) | 6.5 |
| Behenyl alcohol | 2.0 |
| Dimethylpolysiloxane 5 cs | 20.0 |
| Dimethylpolysiloxane ($R_{11}$ and $R_{22}$ are methyl groups, n = 7000) | 6.0 |
| 2-Octyldodecanol | 2.0 |
| Polyoxyethylene hydrogenated castor oil derivative (adduct with 60 moles of ethylene oxide) | 0.3 |
| Polyoxyethylene stearyl ether (adduct with 4 moles of ethylene oxide) | 1.0 |
| Soybean lecithin | 0.5 |
| Glycerol | 10.0 |
| Dipropylene glycol | 5.0 |
| Yellow No. 4 (pigment) | q.s. |
| Perfume | q.s. |
| Methyl paraben | q.s. |
| EDTA-3 Na (chelating agent) | q.s. |
| Deionized water | Balance |

The hair treatment cream provided an excellent smoothness, particularly to damaged hair, and exhibited a good hair protective effect.

The present invention provides a hair cosmetic composition able to impart an excellent smoothness to hair during coating, rinsing, drying and after drying, and provides a strong protection of hair from physical damage caused by, for example, brushing, by formulating the components (A), (B) and (C) as described above in a specific quantitative relationship.

We claim:

1. A hair cosmetic composition comprising:
   (A) at least one mono long-chain alkyl quaternary ammonium salt selected from the group consisting of stearyltrimethylammonium chloride and behenyltrimethylammonium chloride;
   (B) at least one higher alcohol selected from the group consisting of cetyl alcohol, stearyl alcohol and behenyl alcohol; and
   (C) at least one high molecular weight silicone having the formula (II):

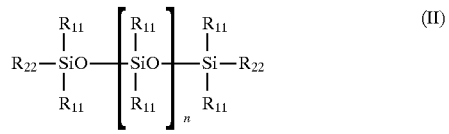

wherein $R_{11}$ represents a methyl group, $R_{22}$ represents a methyl group or hydroxy group, and n is an integer of 5,000 to 20,000, the amount of the component (A) being within the range from 0.1 to 3.0% by weight, based on the total weight of the hair cosmetic composition, the molar ratio of the component (B) relative to the component (A) being within the range of from 3 to 15, and the amount of the component (C) being within the range of from 0.2 to 8% by weight, based on the total weight of the hair cosmetic composition.

2. A hair cosmetic composition as claimed in claim 1, wherein the hair cosmetic contains a liquid oil in an amount necessary for dissolving the high molecular weight silicone.

3. A hair cosmetic composition as claimed in claim 1, wherein said component (C) is at least one high molecular weight silicone having the formula (II), wherein $R_{22}$ represents a methyl group.

4. A hair cosmetic composition as claimed in claim 1, further comprising a humectant.

5. A hair cosmetic composition as claimed in claim 1, further comprising a nonionic surfactant.

6. A hair cosmetic composition as claimed in claim 1, further comprising an amphoteric surfactant.

7. A hair cosmetic composition as claimed in claim 1, further comprising a natural animal extract.

8. A hair cosmetic composition as claimed in claim 1, further comprising a natural vegetable extract.

9. A hair cosmetic composition as claimed in claim 1, further comprising a perfume.

10. A hair cosmetic composition as claimed in claim 1, further comprising a pigment.

11. A hair cosmetic composition as claimed in claim 1, further comprising a preservative.

12. A hair cosmetic composition as claimed in claim 1, further comprising an organic acid.

13. A hair cosmetic composition as claimed in claim 1, further comprising an inorganic acid.

14. A hair cosmetic composition as claimed in claim 1, further comprising a chelating agent.

15. A hair cosmetic composition as claimed in claim 1, further comprising a UV-ray absorber.

16. A hair cosmetic composition as claimed in claim 1, wherein n is 7,000.

17. A hair cosmetic composition as claimed in claim 1, wherein n is 5,000.

* * * * *